United States Patent [19]

Gans et al.

[11] Patent Number: 4,623,667

[45] Date of Patent: Nov. 18, 1986

[54] TOPICAL TREATMENT OF SKIN INFLAMMATORY DISORDERS

[75] Inventors: Eugene Gans, Westport; Sergio Nacht, Weston; David Yeung, Stamford, all of Conn.

[73] Assignee: Richardson-Vicks Inc., Wilton, Conn.

[21] Appl. No.: 749,766

[22] Filed: Jun. 28, 1985

Related U.S. Application Data

[63] Continuation of Ser. No. 521,950, Aug. 10, 1983, abandoned.

[51] Int. Cl.[4] ............................................. A61K 31/01
[52] U.S. Cl. ..................................... 514/762; 424/95; 514/859; 514/887
[58] Field of Search ...................... 514/859, 887, 762; 424/95

[56] References Cited

U.S. PATENT DOCUMENTS 4,229,468  10/1980  Miyao et al. ...................... 424/287

OTHER PUBLICATIONS

Downing et al, Australian J. Chem., 14: 253–263, 1961.
Chemical Abstracts 77: 77040k, 1972 (Matsumoto et al).
Chemical Abstracts 68: 14309y, 1968 (Khalique et al).

*Primary Examiner*—Leonard Schenkman
*Attorney, Agent, or Firm*—Salvatore R. Conte

[57] ABSTRACT

Method and pharmaceutical composition for topically treating skin inflammatory disorders by administering to the inflamed area a therapeutically effective amount of a substantially non-polar hydrocarbon fraction from beeswax comprising a mixture of (i) a major proportion of saturated straight chain $C_{21}$–$C_{33}$ hydrocarbons and (ii) a minor proportion of mono-unsaturated long chain hydrocarbons.

8 Claims, No Drawings

TOPICAL TREATMENT OF SKIN INFLAMMATORY DISORDERS

This is a continuation of application Ser. No. 521,950 filed Aug. 10, 1983 now abandoned.

This invention relates to the discovery that a certain beeswax fraction affords an effective topical treatment for certain inflammatory skin conditions.

Beeswax is the yellow or white (bleached) wax obtained from the honeycomb of the bee and consists largely of myricyl palmitate, cerotic acid and esters, and some high-carbon paraffins and mono-unsaturated long-chain hydrocarbons (monoenes). Trace amounts of triacontanol, i.e., myricyl alcohol, may also be present although this alcohol is predominantly in the form of the palmitate ester.

It has now been found that a certain fraction of beeswax possesses substantial vasoconstrictive activity suitable for topically treating inflammation in humans or animals. This fraction consists essentially of a mixture of the non-polar saturated and mono-unsaturated long-chain hydrocarbons found in beeswax. Analysis of this fraction indicates the presence of about 90% w/w of saturated straight chain hydrocarbons with chain lengths ranging from $C_{21}$ to $C_{33}$, as represented by the formula:

$$CH_3-(CH_2)_n-CH_3 \qquad (I)$$

wherein n is an integer from 19 to 31, with the remainder of the fraction, about 10% w/w, being mono-unsaturated straight chain hydrocarbons of similar chain lengths as in Formula (I). The exact location of the single unsaturated bond in the latter monoenes has not been determined.

The aforementioned hydrocarbon fraction is substantially devoid, that is, containing less than 5% w/w of the polar constituents found in beeswax, such as, for example, myricyl palmitate, cerotic acid and its esters and the like.

According to D. T. Downing et al. Australian J. Chem. 14:253–263, 1961, the makeup of the naturally occurring hydrocarbons in beeswax is approximately as follows in percent by weight:

| n-Paraffin Hydrocarbon Carbon No. | Naturally Occurring Hydrocarbons | | |
|---|---|---|---|
| | Wax A | Wax B | Average |
| 19 | 0.5 | 0.3 | 0.4 |
| 20 | | | |
| 21 | 0.8 | 0.8 | 0.8 |
| 22 | 0.3 | 0.2 | 0.25 |
| 23 | 3.7 | 3.7 | 3.7 |
| 24 | 0.6 | 0.4 | 0.5 |
| 25 | 7.5 | 8.8 | 8.15 |
| 26 | 1.2 | 1.1 | 1.1 |
| 27 | 26.8 | 30.1 | 28.45 |
| 28 | 2.2 | 1.3 | 1.75 |
| 29 | 19.3 | 16.5 | 17.9 |
| 30 | 1.6 | 0.9 | 1.25 |
| 31 | 20.8 | 19.0 | 19.9 |
| 32 | 0.9 | 1.5 | 1.2 |
| 33 | 13.8 | 15.5 | 14.65 |
| | 100.0 | 100.0 | 100.00 |

The subject hydrocarbon fraction has been found to be therapeutically effective in treating inflammation of the skin, including acne. For purposes of this disclosure, the term "treating acne" is used to mean the temporary alleviation of the inflammation of the affected skin and other inflammatory signs and symptoms associated with acne.

In additon to treating acne, the superior vasoconstrictor activity of the subject hydrocarbon fraction affords its usage as an effective anti-inflammatory treatment for the following skin disorders: atopic dermatitis, atopic eczema, herpes simplex, shingles, poison ivy, poison oak, poison sumac and other skin allergic reactions, psoriasis, dandruff and the like. As with acne, the term "anti-inflammatory treatment" or its equivalent is used to mean the temporary alleviation of the inflammation of the affected skin and other inflammatory signs and symptoms associated with the particular skin disorder.

Suitable pharmaceutical carriers for the topical administration of the subject hydrocarbon fraction are non-polar pharmaceutical vehicles in conventional forms such as solutions, lotions, emulsions, ointments, gels, etc., in which the pharmaceutical carrier merely provides a physical form for the effective topical application of the active hydrocarbon fraction to the skin. The therapeutic composition is prepared by simply mixing the desired therapeutically effective amount of the hydrocarbon fraction with the particular carrier according to conventional pharmaceutical compounding techniques.

By a "therapeutically effective amount" is meant an amount which is effective to alleviate the inflammation of the dermatological condition and yet cause substantially no undesirable side effects (at a reasonable benefit/risk ratio). In general, the hydrocarbon fraction is therapeutically effective in from about 0.1 to about 10 percent by weight, based on the composition weight, with amounts from about 0.5 to about 5 percent by weight being preferred.

The isolation of the subject hydrocarbon fraction from beeswax is illustrated in the following example using column chromatography on silica gel with hexane as the elution solvent:

EXAMPLE 1

A glass column 50 cm in length and 3 cm in diameter was dry-packed with Silica Gel 60 of particle size 0.063–0.200 mm (70–230 mesh ASTM); purchased from E. Merck Chemical Co. The Silica Gel was oven-dried at 120° C. for 4 to 6 hours prior to use. 50 Grams of beeswax (yellow wax obtained from honeycombs) was dissolved in 500 mls of warm hexane and the mixture was passed through the column at ambient temperature. The eluent was collected in a suitable glass vessel. The column was then eluted with an additional 1000 mls of hexane. The eluents were pooled and evaporated to dryness under vacuum using a rotoevaporator, affording the hydrocarbon fraction of this invention as off-white crystals, m.p.=51° C.

In addition to hexane, which is preferred, other non-polar organic solvents may be used to extract the hydrocarbon fraction from beeswax such as, for example, an aliphatic alkane such as pentane, heptane and the like; an aromatic hydrocarbon such as benzene, toluene, xylene and the like; an ether such as diethyl ether, dioxane and the like; tetrahydrofuran; nd the like aprotic solvents. With such aprotic solvents as eluents, it is perferred to use a polar stationing phase such as, for example, silica gel, in the chromatographic separation step.

Accordingly, the subject hydrocarbon fraction may be derived from beeswax by:

(a) dissolving beeswax in an organic aprotic solvent;

(b) chromatographically separating out of said beeswax solution substantially all of the polar constituents of beeswax;

(c) collecting the chromatographic eluent containing the non-polar hydrocarbon fraction, and (d) evaporating the organic solvent from said eluent to yield the substantially non-polar hydrocarbon fraction.

The chemical analysis of the hydrocarbon fraction obtained from Example 1 is demonstrated in the following two examples.

EXAMPLE 2

Thin Layer Chromotography (TLC): 5 microliters of chloroform containing 10 to 20 ug of the material to be tested is spotted on a 20×20 cm, 250 micron silica gel G plate. The plate is developed in toluene once, air dried and sprayed with 50% sulfuric acid. The plate is then charred on a hot plate at 220° C. All carbon containing materials appear as dark brown to black spots and the amount of carbon containing materials correlates with the intensity of the spot. Identification of compounds is accomplished by comparing the mobility of compounds to that of authentic standards. Analysis of the hydrocarbon fraction obtained from Example 1 by this TLC technique revealed the presence of >95% hydrocarbons with <5% polar materials at the origin.

EXAMPLE 3

Gas Liquid Chromatography (GLC): GLC analysis was performed on a column packed with 3% SE-30 (80/100 mesh). Temperature programming was from 120° C.–300° C. at a rate of 5° C./minute. 2 Microliters of the sample was injected and detection was accomplished by flame ionization. Identification of the chain length distribution of the beeswax derived hydrocarbon was accomplished by direct comparison of its chromatogram with that of a series of normal paraffins of even carbon number $C_{14}$ through $C_{34}$ and the plotting or retention times against the carbon number. Analysis of the hydrocarbon fraction obtained from Example 1 by this GLC technique shows a content of about 90% saturated straight chain hydrocarbons with chain length ranging from $C_{21}$ to $C_{33}$ and about 10% mono-unsaturated hydrocarbons of similar chain length.

The instant invention thus provides a pharmaceutical composition for alleviating inflammation associated with skin disorders comprising a therapeutically effective amount of a substantially non-polar hydrocarbon fraction derived from beeswax and a pharmaceutical carrier suitable for topical administration, said beeswax fraction consisting essentially of (i) more than 95 percent by weight of a hydrocarbon mixture consisting essentially of about 90 percent by weight of saturated straight chain hydrocarbons and about 10 percent by weight of mono-unsaturated hydrocarbons, wherein the chain length of said hydrocarbons is from $C_{21}$ to $C_{33}$, and (ii) less than 5 percent by weight of polar constituents in beeswax.

A particularly suitable pharmaceutical carrier in ointment form for purposes of this invention is Hydrophilic Ointment U.S.P., an oil-in-water emulsion ointment base having the formulation:

| | |
|---|---|
| Methylparaben | 0.25 g |
| Propylparaben | 0.15 g |
| Sodium lauryl sulfate | 10 g |
| Propylene glycol | 120 g |
| Stearyl alcohol | 250 g |
| White petrolatum | 250 g |
| Purified water | 370 g |
| To make about . . . | 1000 g |

To stearyl alcohol and the white petrolatum are melted on a steam bath and warmed to about 75° C. The other ingredients are dissolved in the purified water and also heated to 75° C. The petrolatum phase is then added to the water phase with mixing until the mixture congeals. The resultant ointment is cooled to room temperature.

The vasoconstriction activity of the subject hydrocarbon fraction is demonstrated in the following in-vivo vasoconstrictor assay, which is a modification of the Stoughton-McKenzie Vasoconstrictor Assay described in "Method for Comparing Percutaneous Absorption of Steroids", Arch. Derm. 86:608–610, 1962.

The test was performed on a defined area of the volar aspect of the forearm in 5 subjects. The test formulations were applied under semi-occlusion to maximize differences in activity. Thus, test formulations were saturated on the absorbent cushion pad of ¾ inch bandages (Curity Curad Sheer Bandages) and the bandages were taped to the forearm with no more than 5 bandages per forearm. The bangages were left on the forearm for 24 hours and then removed. The treatment sites were washed with soap and water to remove any excess material still on the skin surface. After 1 hour, the resulting blanching or whitening of the skin was then scored by two judges using the following scoring system:

0=No blanching
1=Barely perceptible blanching
2=Distinct blanching with well defined outline
3=Strong blanching An increase in blanching reflects a corresponding increase in vasoconstriction activity.

EXAMPLE 4

The experimental results on the activity of the subject hydrocarbon fraction in the foregoing vasoconstriction assay are set forth below. For comparative purposes, a potent commercially available (Syntex Laboratories, Inc.) steroid anti-inflammatory product, LIDEX Cream, containing 0.05% of the active anti-inflammatory compound fluocinonide, was used as a positive control. Also included in the test were an alcohol extract from beeswax containing the polar constituents of beeswax itself, and triacontanol (myricyl alcohol) Reference Standard (>99% pure). The results tabulated below are averages of at least five subjects. Products B through E were tested at 1% w/w concentration in the previously described Hydrophilic Ointment U.S.P.

| Product | Blanching |
|---|---|
| A. LIDEX Cream 0.05% | 2.5 |
| B. Hydrocarbon fraction obtained from Example 1 | 2.3 |
| C. Alcohol extract of beeswax | 1.1 |
| D. Triacontanol Ref. Std. | 0.5 |
| E. Beeswax (yellow) | 1.0 |

| -continued | |
|---|---|
| Product | Blanching |
| F. Hydrophilic Ointment U.S.P. | 0.6 |

As the results indicate, LIDEX Cream 0.05% induced the highest vasoconstrictive effect with close to a maximum score of 2.5. The subject hydrocarbon fraction from beeswax scored 2.3 in the blanching scale, which, although slightly lower than that of LIDEX Cream 0.05%, is significantly higher than any of the other materials tested. The alcohol extract obtained from beeswax and the unfractionated beeswax are equally effective with a blanching score of 1.1 and 1.0 respectively, indicating only very mild blanching was observed. The hydrophilic ointment vehicle induced a slight blanching effect with a score of 0.6. Pure triacontanol (Reference Standard) was found to have the lowest activity with a score of 0.5; suggesting that it has little or no vasoconstrictor activity.

In view of its marked vasoconstrictor activity, the subject hydrocarbon fraction is deemed to be of value as a therapeutic agent for treatment of inflammatory skin disorders. When the compositions of the present invention are used in the treatment of such disorders, the amount of composition typically applied and treatment regimen will vary, depending upon, for example, the particular disorder being treated and its severity, the frequency of application and the area of the body which is afflicted.

For example, when the compositions of this invention are used in the topical treatment of acne, the preferred treatment will comprise applying a therapeutically effective amount of the composition to the afflicted situs on the skin. Generally, a therapeutically effective amount would be from about 1 mg/cm$^2$ to about 10 mg/cm$^2$ of the composition per day. It is preferred to cleanse the skin prior to treatment. The treatment is more effective if topical applications are made 2 to 4 times daily.

We claim:

1. A method of alleviating inflammation associated with skin disorders which comprises applying topically to the afflicted situs a pharmaceutical composition comprising a therapeutically effective amount of a substantially non-polar hydrocarbon fraction derived from beeswax and a pharmaceutical carrier suitable for topical administration, said beeswax fraction consisting essentially of:
    (i) more than 95 weight percent of a hydrocarbon mixture consisting essentially of about 90 percent saturated straight chain hydrocarbons and about 10 percent mono-unsaturated hydrocarbons, wherein the chain length of said hydrocarbons is from $C_{21}$ to $C_{33}$, and
    (ii) less than 5 weight percent of polar constituents in beeswax.

2. A method of alleviating inflammation associated with skin disorders which comprises applying topically to the afflicted situs a pharmaceutical composition comprising from about 0.1 to about 10 percent by weight, based on the composition weight, of a substantially non-polar hydrocarbon fraction derived from beeswax and a pharamaceutical carrier suitable for topical administration, said beeswax fraction consisting essentially of:
    (i) more than 95 weight percent of a hydrocarbon mixture consisting essentially of about 90 percent saturated straight chain hydrocarbons and about 10 percent mono-unsaturated hydrocarbons, wherein the chain length of said hydrocarbons is from $C_{21}$ to $C_{33}$, and
    (ii) less than 5 weight percent of polar constituents in beeswax.

3. A method of alleviating inflammation associated with acne in a human having skin affected thereby which comprises applying topically to the afflicted situs a pharmaceutical composition comprising a therapeutically effective amount of a substantially non-polar hydrocarbon fraction derived from beeswax and a pharmaceutical carrier suitable for topical administration, said beeswax fraction consisting essentially of:
    (i) more than 95 weight percent of a hydrocarbon mixture consisting essentially of about 90 percent saturated straight chain hydrocarbons and about 10 percent mono-unsaturated hydrocarbons, wherein the chain length of said hydrocarbons is from $C_{21}$ to $C_{33}$, and
    (ii) less than 5 weight percent of polar constituents in beeswax.

4. A method of alleviating inflammation associated with acne in a human having skin affected thereby which comprises applying topically to the afflicted situs a pharmaceutical composition comprising from about 0.1 to about 10 percent by weight, based on the composition weight, of a substantially non-polar hydrocarbon fraction derived from beeswax and a pharmaceutical carrier suitable for topical administration, said beeswax fraction consisting essentially of:
    (i) more than 95 weight percent of a hydrocarbon mixture consisting essentially of about 90 percent saturated straight chain hydrocarbons and about 10 percent mono-unsaturated hydrocarbons, wherein the chain length of said hydrocarbons is from $C_{21}$ to $C_{33}$, and
    (ii) less than 5 weight percent of polar constituents in beeswax.

5. A pharmaceutical composition for alleviating inflammation associated with skin disorders comprising a therapeutically effective amount of a substantially non-polar hydrocarbon fraction derived from beeswax and a pharmaceutical carrier suitable for topical administration in lotion, emulsion, ointment or gel form, said beeswax fraction consisting essentially of:
    (i) more than 95 weight percent of a hydrocarbon mixture consisting essentially of about 90 percent saturated straight chain hydrocarbons and about 10 percent mono-unsaturated hydrocarbons, wherein the chain length of said hydrocarbons is from $C_{21}$ to $C_{33}$, and
    (ii) less than 5 weight percent of polar constituents in beeswax.

6. The composition of claim 5 wherein said pharmaceutical carrier is Hydrophilic Ointment U.S.P.

7. A pharmaceutical composition for alleviating inflammation associated with skin disorders comprising from about 0.1 to about 10 percent by weight, based on the composition weight, of a substantially non-polar hydrocarbon fraction derived from beeswax and a pharmaceutical carrier suitable for topcial administration in lotion, emulsion, ointment or gel form, said beeswax fraction consisting essentially of:
    (i) more than 95 weight percent of a hydrocarbon mixture consisting essentially of about 90 percent saturated straight chain hydrocarbons and about 10 percent mono-unsaturated hydrocarbons, wherein the chain length of said hydrocarbons is from $C_{21}$ to $C_{33}$, and
    (ii) less than 5 weight percent of polar constituents in beeswax.

8. The composition of claim 7 wherein said pharmaceutical carrier is Hydrophilic Ointment U.S.P.

* * * * *